US012758687B2

(12) United States Patent
Prost et al.

(10) Patent No.: US 12,758,687 B2
(45) **Date of Patent: *Oct. 13, 2026**

(54) METHOD FOR PREPARING AN ANTI-ADHESION BARRIER FILM

(71) Applicant: SOFRADIM PRODUCTION, Trevoux (FR)

(72) Inventors: Nicolas Prost, Orlienas (FR); Delphine Petit, Montanay (FR); Xavier Bourges, Mogneneins (FR)

(73) Assignee: SOFRADIM PRODUCTION, Trevoux (FR)

( * ) Notice: Subject to any disclaimer, the term of this patent is extended or adjusted under 35 U.S.C. 154(b) by 113 days.

This patent is subject to a terminal disclaimer.

(21) Appl. No.: 18/813,240

(22) Filed: Aug. 23, 2024

(65) Prior Publication Data

US 2025/0018092 A1 Jan. 16, 2025

Related U.S. Application Data

(63) Continuation of application No. 16/717,112, filed on Dec. 17, 2019, now Pat. No. 12,070,534, which is a continuation of application No. 15/503,758, filed as application No. PCT/EP2015/071823 on Sep. 23, 2015, now Pat. No. 10,549,015.

(30) Foreign Application Priority Data

Sep. 24, 2014 (EP) .................................... 14306475

(51) Int. Cl.

| | |
|---|---|
| ***A61L 31/04*** | (2006.01) |
| ***A61F 2/00*** | (2006.01) |
| ***A61L 27/34*** | (2006.01) |
| ***A61L 27/58*** | (2006.01) |
| ***A61L 31/10*** | (2006.01) |
| ***A61L 31/14*** | (2006.01) |
| ***B29C 41/02*** | (2006.01) |
| ***B29C 41/12*** | (2006.01) |
| ***B29C 41/22*** | (2006.01) |
| ***B29C 41/24*** | (2006.01) |
| ***C08J 5/18*** | (2006.01) |
| ***C08J 7/04*** | (2020.01) |
| ***C08L 89/06*** | (2006.01) |

(52) U.S. Cl.

CPC .......... *A61L 31/044* (2013.01); *A61F 2/0063* (2013.01); *A61F 2/0077* (2013.01); *A61L 27/34* (2013.01); *A61L 27/58* (2013.01); *A61L 31/10* (2013.01); *A61L 31/148* (2013.01); *C08J 5/18* (2013.01); *C08J 7/0427* (2020.01); *C08L 89/06* (2013.01); *A61F 2002/009* (2013.01); *A61L 2400/18* (2013.01); *A61L 2420/08* (2013.01); *B29C 41/02* (2013.01); *B29C 41/12* (2013.01); *B29C 41/22* (2013.01); *B29C 41/24* (2013.01); *C08J 2389/06* (2013.01); *C08J 2489/06* (2013.01)

(58) Field of Classification Search

CPC ...... A61L 31/044; A61L 31/10; A61L 31/148; A61L 27/34; A61L 27/58; A61L 2400/18; A61L 2420/08; A61F 2/0063; A61F 2/0077; A61F 2002/009; B29C 41/02; B29C 41/12; B29C 41/22; B29C 41/24; C08J 7/0427; C08J 5/18; C08J 89/06; C08J 2389/06; C08J 2489/06

See application file for complete search history.

(56) References Cited

U.S. PATENT DOCUMENTS

| | | | |
|---|---|---|---|
| 3,118,294 | A | 1/1964 | Laethem |
| 3,276,448 | A | 10/1966 | Kronenthal |
| 3,320,649 | A | 5/1967 | Naimer |
| 3,364,200 | A | 1/1968 | Ashton et al. |
| 4,006,747 | A | 2/1977 | Kronenthal et al. |
| 4,060,081 | A | 11/1977 | Yannas et al. |
| 4,307,717 | A | 12/1981 | Hymes et al. |
| 4,500,676 | A | 2/1985 | Balazs et al. |
| 4,603,695 | A | 8/1986 | Ikada et al. |
| 4,704,131 | A | 11/1987 | Noishiki et al. |
| 4,769,038 | A | 9/1988 | Bendavid et al. |
| 4,796,603 | A | 1/1989 | Dahlke et al. |
| 4,813,942 | A | 3/1989 | Alvarez |
| 4,854,316 | A | 8/1989 | Davis |
| 4,931,546 | A | 6/1990 | Tardy et al. |
| 4,950,483 | A | 8/1990 | Ksander et al. |
| 5,002,551 | A | 3/1991 | Linsky et al. |

(Continued)

FOREIGN PATENT DOCUMENTS

| | | |
|---|---|---|
| EP | 0372969 A1 | 6/1990 |
| EP | 0552576 A1 | 7/1993 |

(Continued)

OTHER PUBLICATIONS

International Search Report for PCT/EP2015/071823 date of completion is Oct. 6, 2015 (2 pages).

*Primary Examiner* — Robert A Lynch

(74) *Attorney, Agent, or Firm* — Weber Rosselli & Cannon LLP

(57) ABSTRACT

The present disclosure relates to an implantable anti-adhesion barrier film comprising an anti-adhesive compound including an oxidized collagen and a polyphosphate compound. The disclosure further relates to a method of preventing post-surgical adhesions in a patient comprising: implanting an implantable anti-adhesion barrier film comprising an anti-adhesive compound including both oxidized collagen and a polyphosphate compound.

12 Claims, No Drawings

(56) References Cited

U.S. PATENT DOCUMENTS

| | | | | |
|---|---|---|---|---|
| 5,192,301 | A | 3/1993 | Kamiya et al. | |
| 5,201,764 | A | 4/1993 | Kelman et al. | |
| 5,217,493 | A | 6/1993 | Raad et al. | |
| 5,254,133 | A | 10/1993 | Seid | |
| 5,256,418 | A | 10/1993 | Kemp et al. | |
| 5,263,983 | A | 11/1993 | Yoshizato et al. | |
| 5,306,500 | A | 4/1994 | Rhee et al. | |
| 5,328,955 | A | 7/1994 | Rhee et al. | |
| 5,350,583 | A | 9/1994 | Yoshizato et al. | |
| 5,368,549 | A | 11/1994 | Mcvicker | |
| 5,376,375 | A | 12/1994 | Rhee et al. | |
| 5,376,376 | A | 12/1994 | Li | |
| 5,399,361 | A | 3/1995 | Song et al. | |
| 5,413,791 | A | 5/1995 | Rhee et al. | |
| 5,428,022 | A | 6/1995 | Palefsky et al. | |
| 5,433,996 | A | 7/1995 | Kranzler et al. | |
| 5,536,656 | A | 7/1996 | Kemp et al. | |
| 5,565,210 | A | 10/1996 | Rosenthal et al. | |
| 5,580,923 | A | 12/1996 | Yeung et al. | |
| 5,593,441 | A | 1/1997 | Lichtenstein et al. | |
| 5,595,621 | A | 1/1997 | Light et al. | |
| 5,601,571 | A | 2/1997 | Moss | |
| 5,618,551 | A | 4/1997 | Tardy et al. | |
| 5,658,582 | A | 8/1997 | Dorigatti et al. | |
| 5,667,839 | A | 9/1997 | Berg | |
| 5,681,568 | A | 10/1997 | Goldin et al. | |
| 5,686,115 | A | 11/1997 | Vournakis et al. | |
| 5,690,675 | A | 11/1997 | Sawyer et al. | |
| 5,697,978 | A | 12/1997 | Sgro | |
| 5,709,934 | A | 1/1998 | Bell et al. | |
| 5,716,409 | A | 2/1998 | Debbas | |
| 5,766,631 | A | 6/1998 | Arnold | |
| 5,785,983 | A | 7/1998 | Furlan et al. | |
| 5,791,352 | A | 8/1998 | Reich et al. | |
| 5,800,541 | A | 9/1998 | Rhee et al. | |
| 5,843,470 | A | 12/1998 | Reeve et al. | |
| 5,861,034 | A | 1/1999 | Taira et al. | |
| 5,863,984 | A | 1/1999 | Doillon et al. | |
| 5,871,767 | A | 2/1999 | Dionne et al. | |
| 5,876,444 | A | 3/1999 | Lai | |
| 5,931,165 | A | 8/1999 | Reich et al. | |
| 5,962,136 | A | 10/1999 | Dewez et al. | |
| 5,993,844 | A | 11/1999 | Abraham et al. | |
| 5,997,895 | A | 12/1999 | Narotam et al. | |
| 6,004,333 | A | 12/1999 | Sheffield et al. | |
| 6,034,088 | A | 3/2000 | Reeve et al. | |
| 6,042,592 | A | 3/2000 | Schmitt | |
| 6,056,970 | A | 5/2000 | Greenawalt et al. | |
| 6,083,522 | A | 7/2000 | Chu et al. | |
| 6,120,539 | A | 9/2000 | Eldridge et al. | |
| 6,153,292 | A | 11/2000 | Bell et al. | |
| 6,165,488 | A | 12/2000 | Tardy et al. | |
| 6,197,935 | B1 | 3/2001 | Doillon et al. | |
| 6,221,109 | B1 | 4/2001 | Geistlich et al. | |
| 6,224,616 | B1 | 5/2001 | Kugel | |
| 6,258,124 | B1 | 7/2001 | Darois et al. | |
| 6,262,332 | B1 | 7/2001 | Ketharanathan | |
| 6,264,702 | B1 | 7/2001 | Ory et al. | |
| 6,277,397 | B1 | 8/2001 | Shimizu | |
| 6,312,474 | B1 | 11/2001 | Francis et al. | |
| 6,383,201 | B1 | 5/2002 | Dong | |
| 6,391,333 | B1 | 5/2002 | Li et al. | |
| 6,391,939 | B2 | 5/2002 | Tayot et al. | |
| 6,399,624 | B1 | 6/2002 | Reeve et al. | |
| 6,408,656 | B1 | 6/2002 | Ory et al. | |
| 6,410,044 | B1 | 6/2002 | Chudzik et al. | |
| 6,413,742 | B1 | 7/2002 | Olsen et al. | |
| 6,428,978 | B1 | 8/2002 | Olsen et al. | |
| 6,440,167 | B2 | 8/2002 | Shimizu | |
| 6,443,964 | B1 | 9/2002 | Ory et al. | |
| 6,447,551 | B1 | 9/2002 | Goldmann | |
| 6,451,032 | B1 | 9/2002 | Ory et al. | |
| 6,454,787 | B1 | 9/2002 | Maddalo et al. | |
| 6,500,464 | B2 | 12/2002 | Ceres et al. | |
| 6,509,031 | B1 | 1/2003 | Miller et al. | |
| 6,514,286 | B1 | 2/2003 | Leatherbury et al. | |
| 6,540,773 | B2 | 4/2003 | Dong | |
| 6,548,081 | B2 | 4/2003 | Sadozai et al. | |
| 6,554,855 | B1 | 4/2003 | Dong | |
| 6,576,019 | B1 | 6/2003 | Atala | |
| 6,596,304 | B1 | 7/2003 | Bayon et al. | |
| 6,599,524 | B2 | 7/2003 | Li et al. | |
| 6,599,526 | B2 | 7/2003 | Dimitrijevich | |
| 6,599,690 | B1 | 7/2003 | Abraham et al. | |
| 6,652,594 | B2 | 11/2003 | Francis et al. | |
| 6,653,450 | B1 | 11/2003 | Berg et al. | |
| 6,682,760 | B2 | 1/2004 | Noff et al. | |
| 6,706,684 | B1 | 3/2004 | Bayon et al. | |
| 6,730,299 | B1 | 5/2004 | Tayot et al. | |
| 6,743,435 | B2 | 6/2004 | Devore et al. | |
| 6,773,723 | B1 | 8/2004 | Spiro et al. | |
| 6,790,438 | B1 | 9/2004 | Constancis et al. | |
| 6,790,454 | B1 | 9/2004 | Abdul et al. | |
| 6,893,653 | B2 | 5/2005 | Abraham et al. | |
| 6,949,525 | B2 | 9/2005 | Hermida et al. | |
| 6,974,679 | B2 | 12/2005 | Andre et al. | |
| 6,974,862 | B2 | 12/2005 | Ringeisen et al. | |
| 7,025,063 | B2 | 4/2006 | Snitkin et al. | |
| 7,041,868 | B2 | 5/2006 | Greene et al. | |
| RE39,172 | E | 7/2006 | Bayon et al. | |
| 7,098,315 | B2 | 8/2006 | Schaufler | |
| 7,175,852 | B2 | 2/2007 | Simmoteit et al. | |
| 7,214,765 | B2 | 5/2007 | Ringeisen et al. | |
| 7,226,611 | B2 | 6/2007 | Yura et al. | |
| 10,335,257 | B2 | 7/2019 | Rizk et al. | |
| 10,549,015 | B2 * | 2/2020 | Prost | A61L 27/58 |
| 12,070,534 | B2 * | 8/2024 | Prost | A61L 27/34 |
| 2001/0008930 | A1 | 7/2001 | Tayot et al. | |
| 2001/0018618 | A1 | 8/2001 | Ketharanathan | |
| 2001/0053839 | A1 | 12/2001 | Noishiki et al. | |
| 2002/0013408 | A1 | 1/2002 | Rhee et al. | |
| 2002/0049503 | A1 | 4/2002 | Milbocker | |
| 2002/0095218 | A1 | 7/2002 | Carr et al. | |
| 2002/0119177 | A1 | 8/2002 | Bowman et al. | |
| 2002/0120348 | A1 | 8/2002 | Melican et al. | |
| 2002/0127265 | A1 | 9/2002 | Bowman et al. | |
| 2002/0131933 | A1 | 9/2002 | Delmotte | |
| 2003/0013989 | A1 | 1/2003 | Obermiller et al. | |
| 2003/0023316 | A1 | 1/2003 | Brown et al. | |
| 2003/0086975 | A1 | 5/2003 | Ringeisen | |
| 2003/0114937 | A1 | 6/2003 | Leatherbury et al. | |
| 2003/0133967 | A1 | 7/2003 | Ruszczak et al. | |
| 2003/0147935 | A1 | 8/2003 | Binette et al. | |
| 2003/0149173 | A1 | 8/2003 | Rhee et al. | |
| 2003/0152522 | A1 | 8/2003 | Miller et al. | |
| 2003/0193104 | A1 | 10/2003 | Melican et al. | |
| 2003/0203485 | A1 | 10/2003 | Takezawa et al. | |
| 2003/0212460 | A1 | 11/2003 | Darois et al. | |
| 2003/0225355 | A1 | 12/2003 | Butler | |
| 2003/0232746 | A1 | 12/2003 | Lamberti et al. | |
| 2004/0001877 | A1 | 1/2004 | Li et al. | |
| 2004/0002444 | A1 | 1/2004 | Shiba et al. | |
| 2004/0013712 | A1 | 1/2004 | Parma | |
| 2004/0018175 | A1 | 1/2004 | Dimitrijevich | |
| 2004/0037866 | A1 | 2/2004 | Semertzides et al. | |
| 2004/0054406 | A1 | 3/2004 | Dubson et al. | |
| 2004/0059356 | A1 | 3/2004 | Gingras | |
| 2004/0101546 | A1 | 5/2004 | Gorman et al. | |
| 2004/0105880 | A1 | 6/2004 | Turner et al. | |
| 2004/0138762 | A1 | 7/2004 | Therin et al. | |
| 2004/0181288 | A1 | 9/2004 | Darois et al. | |
| 2005/0002893 | A1 | 1/2005 | Goldmann | |
| 2005/0009178 | A1 | 1/2005 | Yost et al. | |
| 2005/0021058 | A1 | 1/2005 | Negro | |
| 2005/0085924 | A1 | 4/2005 | Darois et al. | |
| 2005/0137512 | A1 | 6/2005 | Campbell et al. | |
| 2005/0142161 | A1 | 6/2005 | Freeman et al. | |
| 2005/0148963 | A1 | 7/2005 | Brennan | |
| 2005/0175659 | A1 | 8/2005 | Macomber et al. | |
| 2005/0232979 | A1 | 10/2005 | Shoshan | |
| 2005/0267521 | A1 | 12/2005 | Forsberg | |
| 2006/0094318 | A1 | 5/2006 | Matsuda et al. | |
| 2006/0135921 | A1 | 6/2006 | Wiercinski et al. | |
| 2006/0147501 | A1 | 7/2006 | Hillas et al. | |

(56) References Cited

U.S. PATENT DOCUMENTS

| | | | |
|---|---|---|---|
| 2006/0167561 | A1 | 7/2006 | Odar et al. |
| 2006/0216320 | A1 | 9/2006 | Kitazono et al. |
| 2006/0252981 | A1 | 11/2006 | Matsuda et al. |
| 2007/0031474 | A1 | 2/2007 | Tayot et al. |
| 2007/0161109 | A1 | 7/2007 | Archibald et al. |
| 2007/0280990 | A1 | 12/2007 | Stopek |
| 2012/0197415 | A1 | 8/2012 | Montanari et al. |
| 2014/0257348 | A1 | 9/2014 | Priewe et al. |
| 2014/0257517 | A1 | 9/2014 | Deichmann et al. |
| 2017/0157296 | A1 | 6/2017 | Walmsley et al. |

FOREIGN PATENT DOCUMENTS

| | | | |
|---|---|---|---|
| EP | 0614650 | A2 | 9/1994 |
| EP | 0621014 | A1 | 10/1994 |
| EP | 0625891 | A1 | 11/1994 |
| EP | 0669138 | A2 | 8/1995 |
| EP | 0705878 | A2 | 4/1996 |
| EP | 0774240 | A1 | 5/1997 |
| EP | 0797962 | A2 | 10/1997 |
| EP | 0827724 | A2 | 3/1998 |
| EP | 0836838 | A1 | 4/1998 |
| EP | 0895762 | A2 | 2/1999 |
| EP | 0898944 | A2 | 3/1999 |
| EP | 1216718 | A1 | 6/2002 |
| EP | 0693523 | B1 | 11/2002 |
| EP | 1315468 | A2 | 6/2003 |
| EP | 1484070 | A1 | 12/2004 |
| EP | 1500664 | A1 | 1/2005 |
| EP | 1561480 | A2 | 8/2005 |
| EP | 1782848 | A2 | 5/2007 |
| FR | 2244853 | A1 | 4/1975 |
| FR | 2715405 | A1 | 7/1995 |
| FR | 2724563 | A1 | 3/1996 |
| WO | 8908467 | A1 | 9/1989 |
| WO | 9311805 | A1 | 6/1993 |
| WO | 9318174 | A1 | 9/1993 |
| WO | 9518638 | A1 | 7/1995 |
| WO | 9608277 | A1 | 3/1996 |
| WO | 9614805 | A1 | 5/1996 |
| WO | 9641588 | A1 | 12/1996 |
| WO | 9729715 | A1 | 8/1997 |
| WO | 9735533 | A1 | 10/1997 |
| WO | 9834656 | A1 | 8/1998 |
| WO | 9849967 | A1 | 11/1998 |
| WO | 9906079 | A1 | 2/1999 |
| WO | 9906080 | A1 | 2/1999 |
| WO | 9951163 | A1 | 10/1999 |
| WO | 0016821 | A1 | 3/2000 |
| WO | 0115625 | A1 | 3/2001 |
| WO | 03002168 | A1 | 1/2003 |
| WO | 2004078120 | A2 | 9/2004 |
| WO | 2005112820 | A2 | 12/2005 |
| WO | 2006018552 | A1 | 2/2006 |
| WO | 2006023444 | A2 | 3/2006 |
| WO | 2007048099 | A3 | 9/2010 |
| WO | 2011026987 | A1 | 3/2011 |

* cited by examiner

METHOD FOR PREPARING AN ANTI-ADHESION BARRIER FILM

CROSS-REFERENCE TO RELATED APPLICATIONS

This application a continuation of U.S. patent application Ser. No. 16/717,112 filed Dec. 17, 2019, which is a continuation of U.S. patent application Ser. No. 15/503,758 filed Feb. 14, 2017, now U.S. Pat. No. 10,549,015, which is a National Stage Application of PCT/EP2015/071823 under 35USC § 371(a), which claims benefit of and priority to European Patent application Ser. No. 14/306,475.6 filed Sep. 24, 2014, and the disclosures of each of the above-identified applications are hereby incorporated by reference in their entirety.

The present invention concerns a method for preparing a film for preventing postsurgical adhesions, as well as the film obtainable by this method. The film of the invention finds application in the field of visceral or parietal surgery. In particular, the film of the invention may be used in association with a prosthetic fabric, as a coating of the fabric, for forming a composite implant intended to be used in parietal surgery, in the repair of eventrations or hernias. The present invention further relates to surgical implants comprising such a film.

Postsurgical adhesions include all non-anatomical fibrous connections accidentally induced by a surgical act during the normal process of healing. They may occur in all surgical disciplines regardless of the operation in question. They are generally all the more severe, the greater the surgical trauma and the more affected the tissues which normally ensure the planes of division (interstitial connective tissue, the synovial membranes, the tendon sheaths, peritoneal and pleural serosa, etc.). Any surgical trauma to tissue is followed by a cascade of physiological events, the main times of which can be simplified as follows:

- time zero (t0): surgical trauma, capillary invasion;
- time zero (t0) plus a few minutes: coagulation, formation of fibrin network, release of chemotactic factors;
- time zero (t0) plus 12 to 48 hours: influx of leukocytes, predominantly polynuclears;
- time zero (t0) plus 24 hours to 5 days: influx of leukocytes, predominantly macrophages;
- time zero (t0) plus 4 to 8 days: influx of fibroblasts;
- time zero (t0) plus 5 to 14 days: conjunctive differentiation of the cicatricial reaction;
- time zero (t0) plus 15 to 180 days: cicatricial remodeling.

Although some of the exact mechanisms are still unknown, particularly as regards determination of the intensity of the reaction, it appears that the first few days are decisive since they condition the influx of fibroblasts responsible for the formation of adhesions.

For this reason, such postsurgical adhesions can induce syndromes such as chronic pain, occlusive syndromes and female infertility. Furthermore, they increase very substantially the risks of making errors in follow-up surgery (myocardial or intestinal invasion during repeat thoracotomy or laparotomy), while prolonging the operating times, since the preliminary dissection can be very awkward in such cases.

One solution to this problem consists in interposing a physical barrier between the structures which must not be involved in any adhesion process. Such a physical barrier should anyway show a substantially smooth and nonporous surface, so as not to offer space for cell recolonization and therefore to limit the original cell adhesion.

In order to remedy this problem, hydrophobic and inert artificial polymers have been used, for example expanded PTFE, or absorbable polymer substances, for example those based on hyaluronates, or on modified cellulose, which substances rapidly form a hydrogel by hydration in the body.

Nevertheless, and in particular in visceral and parietal surgery, but also in orthopedic or neurological surgery, the barrier must also have a certain mechanical strength allowing it to fulfill its function as an element of surgical reconstruction and allowing it to be manipulated by the surgeon while limiting the risks that the barrier be damaged. It is also preferable that the barrier show a certain conformability so as to be capable of following the deformations of the implant it is optionally associated with to during the movements of patient.

Prosthetic fabrics used in the treatment of parietal insufficiencies, for example hernias and eventrations, afford an additional mechanical strength to the surgical reconstruction. Such fabrics are usually made from porous textile such as meshes in order to favor cell colonization.

Surgical implants for use in the treatment of hernia therefore usually comprise a porous prosthetic fabric coated on one of its side with an anti-adhesion barrier. For example, the porous side of the implant is intended to face the abdominal wall to be repaired, for favoring cell colonization, while the anti-adhesion barrier is intended to face the abdominal cavity so as to avoid post-surgical adhesions.

Anti-adhesion barriers based on films comprising collagenous material are known. Such films are bioresorbable. Indeed, in order to avoid post surgery inflammation, it is advised that the material forming the barrier be rapidly absorbed by the biological tissues after the surgical operation.

There is still a need for a physical barrier for preventing postsurgical adhesions, capable of showing good tensile strength so as to be easily handlable by the surgeon, resistant to potential tearing by sutures, and to have a good conformability. In addition, it is desirable that such a physical barrier be capable of being used as a coating for a prosthetic fabric for example. For example, there is the need of an anti-adhesion barrier such as a film that could be used on its own or as a coating of a prosthetic fabric such as a mesh in order to form a surgical implant for hernia repair.

The present invention meets this need by proposing a surgical anti-adhesion barrier film and a method for preparing such a film, the film being usable on its own or as a coating of a prosthetic fabric and showing a particular good tensile strength.

A first aspect of the invention is a method for preparing a surgical anti-adhesion barrier film comprising the following steps:

a°) a first solution, comprising an oxidized collagen at a concentration ranging from 0.5% to 6%, by weight with respect to the total weight of the solution, is prepared, b) a polyphosphate compound is added to the solution of a) in a quantity so as to obtain a concentration of polyphosphate ranging from 0.007 to 0.7%, by weight, with respect to the total weight of the solution, c) the pH of the solution obtained in b) is adjusted to about 9 by addition of a base or to about 5.1 by addition of an acid, d) a diluted solution is prepared by adding water to solution of c) so as to obtain a concentration of oxidized collagen ranging from 0.1% to 2.7%, by weight, with respect to said diluted solution, e) a first layer of solution obtained in c) is casted on an inert support at a basis weight ranging from 0.03 to 0.4 g/$cm^2$, f) before complete gelation of the layer obtained in e), a second layer, of diluted solution obtained in d) is applied on top of said first layer at a basis weight ranging from 0.03 to 0.4 g/$cm^2$, and let to gelify, g) the gelified first and second layers are dried to obtain a film.

Another aspect of the invention is a film obtainable by the method above.

A further aspect of the invention is a surgical implant, for example usable in the treatment of hernia, comprising a biocompatible prosthetic fabric, wherein said prosthetic fabric is at least partially coated with a film obtainable according to the method above.

The method of the invention makes it possible to produce an anti-adhesion barrier film showing a very good tensile strength. In particular, the film obtained by the method of the invention is prepared from a solution comprising a specific collagen, namely an oxidized collagen, and a polyphosphate compound. The film obtained by the method of the invention shows an improved tensile strength compared to films of the prior art based on conventional collagen. In addition, the film obtained by the method of the invention may also show a good elongation at break allowing it to have a good conformability.

According to a first step of the method according to the invention, step a), a solution comprising oxidized collagen is prepared.

The collagen used can be of human or animal origin or may be obtained by genetic recombination means. It may particularly be type I porcine or bovine collagen, or type I or type III human collagen or mixtures in any proportions of the last two types. Native collagen may advantageously be used, in acid solution or after processing, to eliminate the telopeptides, notably by pepsin digestion.

To obtain oxidized collagen, the collagen can be modified by oxidative cleavage using any technique known to those skilled in the art, including, but not limited to the use of periodic acid or one of its salts as described by Tardy et al. in U.S. Pat. No. 4,931,546. Briefly, this technique involves mixing the collagen in acid solution with a solution of periodic acid or one of its salts at a concentration of between 1 and $10^{-5}$ M, in embodiments between 5 $10^{-3}$ and $10^{-1}$ M, at a temperature of between 10 and 25° C. for 10 minutes to 72 hours. This process breaks down hydroxylysine and the sugars of the collagen, thus creating reactive sites without causing crosslinking.

The oxidative cleavage of collagen allows moderate cross-linking later in the collagenic material. It should of course be understood that this function may be provided by other means of moderate cross-linking, for example by beta or gamma irradiation, or other agents of moderate cross-linking, for example chemical reagents at suitably low and non-toxic doses. In embodiments, the oxidized collagen is crosslinked, in particular self crosslinked.

Preparation of oxidized collagen is also described in U.S. Pat. No. 6,706,684, in particular at example 4 of this document, and in WO98/34656, in particular at example 1 of this document.

According to the invention, the concentration of oxidized collagen ranges from 0.5% to 6% by weight with respect to the total weight of the solution. Preferably, the concentration of oxidized collagen is 2.7% by weight with respect to the total weight of the solution.

In embodiments, glycerol is added to solution of step a) at a concentration ranging from 0.1% to 1.5%, preferably of 0.9%, by weight with respect to the total weight of the solution.

In embodiments, polyethylene glycol is added to solution of step a) at a concentration ranging from 0.1% to 1.5%, preferably of 0.9%, by weight with respect to the total weight of the solution.

In embodiments, the glycerol is added to solution of step a) at a concentration ranging from 0.1% to 1.0% by weight with respect to the total weight of the solution, and polyethylene glycol is added to solution of step a) at a concentration ranging from 0.1% to 1.5%, preferably of 0.9%, by weight with respect to the total weight of the solution.

The polyethylene glycol may be selected from polyethylene glycols having a molecular weight ranging from 400 to 6000 Daltons.

The presence of glycerol and/or of polyethylene glycol in the oxidized collagen solution allows obtaining a film showing good handling characteristics. The presence of glycerol and/or of polyethylene glycol in the oxidized collagen solution allows limiting the potential brittling of the film obtained.

According to a second step of the method of the invention, step b), a polyphosphate compound is added to the solution of a) in a quantity so as to obtain a concentration of polyphosphate ranging from 0.007 to 0.7%, by weight, with respect to the total weight of the solution.

Polyphosphates are linear inorganic polyanionic polymer containing few to several hundred residues of orthophosphates which are linked by energy-rich phosphoanhydride bonds. Polyphosphates are frequently used in the daily life as chelating salts as sweeteners for food as bacteriostatic, buffer, antioxidant and protein stabilizes. The safety of the polyphosphate for the living body has long been confirmed, and it is known to be a biodegradable substance that degrades in vivo into atoxic phosphoric acids.

Polyphosphates are present in living organisms. They participate in the formation of channels across the living cell membrane. They handle the environmental conditions by providing phosphate and energy reserves of the cells (prokaryotes and eukaryotes). They are present in animal cells (participation in the regulatory processes during development and cellular proliferation and differentiation), play a key role in blood coagulation (platelet release) and they are source of energy (via adenosine triphosphate).

Polyphosphates compounds suitable for the present invention are salts of polyphosphoric acid, namely compounds having a molecular structure wherein hydrogen of a hydroxyl group of the polyphosphoric acid is substituted with a metal. Examples of the metal in this case include sodium, potassium, calcium and magnesium.

Polyphosphate compounds suitable for the preparation of the film of the present invention may contain one type or multiple types of the above-described polyphosphoric acids or salts thereof. Examples of the multiple types of polyphosphoric acids or salts thereof include polyphosphoric acids having different polymerization degrees or salts thereof, polyphosphoric acids having different molecular structures or salts thereof, and polyphosphate salts having different metal ions. In addition, the polyphosphate compound may contain both polyphosphoric acids and salts thereof.

The polyphosphate compound suitable for the present invention can be at least one type represented by a general formula, $(P_nO_{3n+1})^{(n+2)}$— (wherein "n" indicates an integer between 2 and 5000) associated with a metal selected from sodium, potassium, calcium and magnesium.

In embodiments, the polyphosphate compound used in the preparation of the film of the invention is a sodium polyphosphate. Preferably, the polyphosphate compound is a sodium polyphosphate having a degree of polymerization (n) varying from 2 to 100, more preferably varying from 2 to 25, and more preferably varying from 5 to 25. Films of the invention prepared from sodium polyphosphate having a degree of polymerization varying from 5 to 25 show a particularly good elongation at break. Such films therefore show a good conformability and are capable once implanted of following the deformations of the biological tissues they are adjacent to, or of the prosthetic fabric they are coated on.

Preferred polyphosphates to be used in the present invention are selected from the group consisting in pentasodium tripolyphosphate ($Na_5P_3O_{10}$), sodium hexametaphosphate having a degree of polymerization of 13 $(NaPO_3)_{13}$, sodium hexametaphosphate having a degree of polymerization of 25 $(NaPO_3)_{25}$, and mixtures thereof.

The addition of the polyphosphate compound to the oxidized collagen solution of a) in a quantity so as to obtain a concentration of polyphosphate ranging from 0.007 to 0.7%, by weight, with respect to the total weight of the solution allows the formation in the solution of a soluble ionic complex oxidized collagen/polyphosphate compound. The solution obtained in the present step b) is therefore homogeneous and will enable the formation of a homogeneous film in the subsequent steps of the method.

According to a third step of the method of the invention, step c), the pH of the solution obtained in b) is adjusted to about 9 by addition of a base or to about 5.1 by addition of an acid.

It is known that the extractible pH after sterilization of polymeric films is dependent on the method of sterilization used. The films of the invention may be sterilized for example by ethylene oxide or by gamma radiation. In addition, it is advisable that the sterilized films show an extractible pH after sterilization of about 7 in order to maintain good mechanical properties of the film and in order to obtain films suitable for implantation in a human body. In this view, when it is intended to sterilize the film by ethylene oxide, it is advised to set the pH of the oxidized collagen/polyphosphate solution at pH 5.1 in order to obtain a pH around 7 after sterilization. On the contrary, when it is intended to sterilize the film by gamma radiation, it is advised to set the pH of the oxidized collagen/polyphosphate solution at pH 9 in order to obtain a pH around 7 after sterilization.

During the present step c), the pH of the solution may be adjusted to 9 by addition of the adequate amount of base, for example NaOH (1N). Alternatively, the pH of the solution may be adjusted to 5.1 by addition of the adequate amount of acid, for example HCl (1N).

According to a fourth step of the method of the invention, step d), a diluted solution is prepared by adding water to solution of c) so as to obtain a concentration of oxidized collagen ranging from 0.1% to 2.7%, preferably of 1.75%, by weight, with respect to said diluted solution.

The diluted solution thus prepared is intended to be used for the casting of the film, in a further step, step f). As such, the present step d) of preparation of the diluted solution may be completed at any time between step a) and step f).

The solution of step c) and the diluted solution of step e) are intended to be used in two superposed thin layers for the formation of the film of the invention. These thin layers have generally a very low thickness, for example ranging from 1 to 100 μm and are for example obtained by depositing a determined weight of solution per a determined surface area. In this view, one defines a basis weight of these thin layers, similar to a bidimensional or surface density, expressed in g/cm$^2$.

As such, according to a fifth step of the method of the invention, step e), a first layer of solution obtained in c) is casted on an inert support at a basis weight ranging from 0.03 to 0.4 g/cm$^2$, preferably of about 0.11 g/cm$^2$.

The inert support may be a flat hydrophobic support of dimensions adapted to the desired dimensions of the resulting film.

After the first layer has partially gelled by cooling, for example, after 45 min at a temperature of 20° C., a second thin layer is applied to its surface, this being based on the diluted solution. As such, according to a sixth step of the method of the invention, step f), before complete gelation of the layer obtained in e), a second layer, of diluted solution obtained in d) is applied on top of said first layer at a basis weight ranging from 0.03 to 0.4 g/cm$^2$, preferably of about 0.064 g/cm$^2$.

The first and second layers are then let to gelify. The gelation may take between 5 and 45 minutes at a temperature of around 20° C.

According to a seventh step of the invention, step g), the gelified first and second layers are dried to obtain a film. The drying may be completed under laminated flow at 20° C., with a hygrometric degree of 40% and for about 20 hours.

In embodiments, wherein in step c) the pH of the solution obtained in b) is adjusted to about 9, the film obtained at g) is further sterilized by gamma radiation. For example, the film may be submitted to gamma radiation with a dose ranging from 25 to 50 kGy.

In alternative embodiments, wherein in step c) the pH of the solution obtained in b) is adjusted to about 5.1, the film obtained at g) is further sterilized by ethylene oxide. For example, the film is sterilized by ethylene oxide at 30° C. for 12 hours.

Films of the invention sterilized by ethylene oxide show an improved elongation at break compared to films of the invention which are sterilized by gamma radiation. As a consequence, when films showing a certain elasticity will be needed, it will be preferable to sterilize the films of the invention by ethylene oxide. Such films with elastic properties may be needed for example for use in combination with an elastic prosthetic fabric, or simply for their good conformability allowing them to smoothly follow the deformations of the surrounding biological tissues.

In embodiments, and regardless of the method of sterilization used, the sterilized film may be cured in order to reinforce its mechanical properties. For example, the sterilized film is baked at 40° C. for 48 hours.

The film obtained by the method of the invention is preferably continuous, smooth and nonporous.

The film obtained by the method of the invention is bioabsorbable. In the present application, "bioabsorbable" is understood to mean that the materials having this property are absorbed and/or degraded by the tissues or washed from the implantation site and disappear in vivo after a certain time, which may vary, for example, from a few hours to a few months, depending on the chemical nature of the materials.

The rapid absorption of the film obtained by the method of the invention ensures protection against the initial adhesive phenomena, that is to say in the first week following surgery, or in other words during the period of time necessary for the integration of the opposite surface.

The films of the invention may be used on their own as anti-adhesive barriers to be implanted in a patient for preventing post-surgical adhesions. The films of the invention show a good tensile strength and may therefore easily be manipulated by surgeons during a surgical operation. In addition, thanks to their good tensile strength, the films of the invention also offer a good resistance to potential tearing by sutures and fixation devices as tacks, when they are fixed to biological tissues. The films of the invention further show a good elongation at break conferring them a good flexibility and may therefore be particularly useful in case a good conformability is needed.

The films of the invention may also be used in combination with any medical device necessitating an anti-adhesive barrier. For example, the films of the invention may be associated to a biocompatible prosthetic fabric in order to manufacture a composite implant for the treatment of hernias.

A prosthetic fabric may comprise, for example, two opposed porous faces, separated from each other by the thickness of said fabric, but connected to each other by linking yarns. The prosthetic fabric may be bioabsorbable or permanent.

The film of the invention may be coated on one face of the prosthetic fabric, either during the manufacturing of the film, or thereafter. The film may be linked at least on the surface of a face of the prosthetic fabric, and preferably over a certain thickness, for example by capillary absorption of the constituent fibers in the prosthetic fabric. The film may entirely cover a face of the prosthetic fabric, and more preferably projects beyond the edges of the latter in such a way as to protect the resulting implant from visceral contacts, the overlap being from 5 to 10 millimeters for example.

Advantageously, the thickness of the film is less than the thickness of the prosthetic fabric, for example between 2% and 20% of the total thickness of the composite implant.

For example, as a result, the surgical implant of the invention may comprise two faces which are different in their respective appearances and functions, namely one face which is porous or open on one side, in order to accommodate and direct the postsurgical cell colonization, and the other face which is closed by the film of the invention, for tissue separation without adhesion.

Because of its good elongation at break and resulting good flexibility, the film of the invention preserves the manipulability of the implant when it is associated to a prosthetic fabric. The implant may therefore be implanted by the coelioscopic route.

The advantages of the present invention will more clearly appear from the examples below.

EXAMPLES

In the examples below, parts and percentages are by weight unless otherwise indicated.

Example 1

In the present example, films of the invention comprising oxidized collagen and a polyphosphate at various concentrations are prepared. The influence of the type of sterilization (either by ethylene oxide or by gamma radiation) on the elongation at break of the resulting films is studied.

1°) Preparation of the Solutions:

A solution of oxidized collagen is prepared according to example 4 of U.S. Pat. No. 6,706,684 with a final concentration of oxidized collagen of 4.1%. The solution is heated at 37° C. A glycerol solution in water is prepared at 10%. The oxidized collagen solution is diluted with the glycerol solution at a proportion of 88/12. Initial pH is around 3.3 and is then adjusted to 8.94 with a NaOH solution (1N). The solution of oxidized collagen/glycerol is diluted with water to obtain a final concentration of oxidized collagen equal to 2.7% and a final concentration of glycerol equal to 0.9%.

Solutions S1-S5 are then prepared by adding to the solution above sodium hexametaphosphate with a degree of polymerization equal to 13 ($(NaPO_3)_{13}$) in various concentrations, so as to obtain the final concentrations of $(NaPO_3)_{13}$ in the solution as shown in the table below:

| Solution | Final concentration of $(NaPO_3)_{13}$ in % |
|---|---|
| S1 | 0.007 |
| S2 | 0.07 |
| S3 | 0.11 |
| S4 | 0.22 |
| S5 | 0.7 |

It is known that the extractible pH after sterilization of the films is dependent on the type of sterilization used. In this view, when it is intended to sterilize the film by ethylene oxide, it is advised to set the pH of the solution at pH 5.1 in order to obtain a pH around 7 after sterilization. On the contrary, when it is intended to sterilize the film by gamma radiation, it is advised to set the pH of the solution at pH 9 in order to obtain a pH around 7 after sterilization.

In this view, depending on the intended type of sterilization, solutions S1-S5 were readjusted either to pH 9 with addition of NaOH solution (1N), or to pH 5.1 by addition of HCl (1N) and are respectively referred to as S'1, S'2, S'3, S'4 and S'5. For each of these solutions, diluted solutions at 1.75% of oxidized collagen by addition of water are prepared and respectively referred to as S"1, S"2, S"3, S"4 and S"5.

2°) Manufacture of the Films:

A film F1 is prepared according to the following method: a first layer of solution S'1 is casted on an inert support at a basis weight of 0.11 g/cm$^2$. Before complete gelation of this first layer, for example after 45 min, a second layer, of diluted solution S"1, is applied on top of the first layer at a basis weight of 0.064 g/cm$^2$.

After gelation of the two layers, the whole is dried under laminated flow at 20° C., hygrometric degree of 40% for 20 hours. A film F1 is obtained.

Films F2, F3, F4 and F5 are prepared in the same manner with respectively solutions S'2-S'5 and S"2-S"5.

3°) Sterilization and Curing:

Sterilization by Ethylene Oxide:

Films F1-F5 obtained at step 2°) from solutions of pH 5.1 were sterilized by ethylene oxide at 30° C. for 12 hours. The films are then cured at 40° C. for 48 hours.

Sterilization by Gamma Radiation

Films F1-F5 obtained at step 2°) from solutions of pH 9 were sterilized by gamma radiation with a dose of 25 kGy. The films are then cured at 40° C. for 48 hours.

4°) Mechanical Tests:

The tensile strength and elongation at break of the above films were evaluated according to the following protocol: for each film, dogbone shaped samples are prepared. Samples are hydrated with a saline solution of NaCl at 0.9% for 5 minutes. Each sample is placed between the jaws (one fixed, one mobile) of a traction machine Tinius Olsen (model Benchtop Tester). The distance between the two jaws is calibrated at 9 cm. The cell measurement limit is 5 N. The preload is fixed at 0.005 N. A constant extension speed of 50 mm/min is then applied to the mobile jaw until the sample breaks.

The tensile strength is the measured force F necessary to achieve breaking of the sample.

The elongation at break is the deformation in percentage of the length of the sample when it breaks.

The results are collated in the table below, in which the values indicated for the elongation at break in percentage correspond to the mean of 20 tests for each film.

| | Elongation at break in % | |
|---|---|---|
| Film | Sterilized by EtO | Sterilized by γ radiation |
| F1 | 95.50 | 65.25 |
| F2 | 103.28 | 75.62 |
| F3 | 110.12 | 78.45 |
| F4 | 118.95 | 77.34 |
| F5 | 139.54 | 93.19 |

These results show that the elongation at break is greater for the films which have been sterilized by ethylene oxide. Therefore sterilization by ethylene oxide may be preferred when films having a greater elongation are needed, depending on the function desired for the film.

Films of the invention prepared in the present example may be used on their own as an anti-adhesive barrier to be implanted in a patient for preventing post-surgical adhesions. Alternatively, these films may be used in combination with a prosthetic fabric in order to manufacture a composite surgical implant. For example, surgical implants for the treatment of hernia may be prepared by coating one face of a prosthetic fabric, such as a mesh, with a film of the present example. The coated film therefore serves as an anti-adhesive barrier for preventing post-surgical adhesions after implantation of the surgical implant.

Example 2

In the present example, comparative films comprising a non oxidized collagen and the same polyphosphate as in Example 1 at various concentrations are prepared and sterilized either by ethylene oxide or by gamma radiation.

The respective tensile strengths of the comparative films and of the films of the invention are compared.

Comparative films are prepared from solutions comprising a polyphosphate and non oxidized collagen.

Solutions of collagen and glycerol with a final concentration of collagen equal to 2.7% and a final concentration of glycerol equal to 0.9% are prepared in the same manner as in Example 1, except for the fact that the oxidized collagen of Example 1 is replaced by a non oxidized collagen. The non oxidized collagen used is a collagen which has been heated to 60° C. but which has not been modified.

Solutions C1-C3 are then prepared by adding to the solution above sodium hexametaphosphate with a degree of polymerization equal to 13 ($(NaPO_3)_{13}$) in various concentrations, so as to obtain the final concentrations of $(NaPO_3)_{13}$ in the solution as shown in the table below:

| Solution | Final concentration of $(NaPO_3)_{13}$ in % |
|---|---|
| C1 | 0.007 |
| C2 | 0.07 |
| C3 | 0.7 |

Like in Example 1, solutions C1-C3 were readjusted to specific pHs depending on the intended type of sterilization and are respectively referred to hereinafter as C'1, C'2, and C'3. Because the non oxidized collagen of the present example is unstable and degrades at pH 9, solutions C1-C3 intended to be used for films intended to be sterilized by gamma radiation were readjusted to pH 7 with addition of NaOH solution (1N). Solutions C1-C3 intended to be used for films intended to be sterilized by ethylene oxide were readjusted to pH 5.1 by addition of HCl (1N). For each of solutions C'1, C'2, and C'3, diluted solutions at 1.75% of non oxidized collagen by addition of water are prepared and respectively referred to as C"1, C"2, and C"3.

Films were prepared in the same manner as in Example 1 from respectively solutions C'1-C'3 and C"1-C"3.

The obtained films are referred to as FC1, FC2 and FC3.

Films FC1, FC2 and FC3 obtained from solutions of pH 5.1 were sterilized by ethylene oxide at 30° C. for 12 hours. The films were then cured at 40° C. for 48 hours.

Films FC1, FC2 and FC3 obtained from solutions of pH 7 were sterilized by gamma radiation with a dose of 25 kGy. The films were then cured at 40° C. for 48 hours.

Mechanical tests were performed on Films FC1-FC3 in the same manner as in Example 1.

The table below compares the results obtained for the tensile strength of films F1, F2 and F5 of the invention of Example 1 and of films FC1, FC2 and FC3 (comparative), for ethylene oxide sterilization on one hand and for gamma radiation sterilization on the other hand. The values indicated for the tensile strength correspond to the mean of 20 tests for each film.

In this table, F1 is to be compared to FC1, F2 is to be compared to FC2 and F5 is to be compared to FC3.

| | Tensile strength (N) | |
|---|---|---|
| Film | Sterilized by EtO | Sterilized by γ radiation |
| F1 (invention) | 1.309 | 1.787 |
| FC1 (comparative) | 0.979 | 0.776 |
| F2 (invention) | 1.531 | 1.541 |
| FC2 (comparative) | 0.281 | 0.804 |
| F5 (invention) | 1.651 | 1.925 |
| FC3 (comparative) | 0.098 | 0.769 |

These results show that the tensile strength of the films of the invention is much greater than that of comparative films prepared from non oxidized collagen, independently from the fact that the films have been sterilized by ethylene oxide or by gamma radiations.

Example 3

In the present example, films of the invention comprising oxidized collagen and phosphate/polyphosphates of various degrees of polymerization and at various concentrations are prepared and further sterilized either by ethylene oxide or by gamma radiation. The influence of the degree of polymerization on the elongation at break of the resulting films is studied.

The films are prepared in the same manner as in Example 1, by varying the phosphate/polyphosphate used. The following phosphate/polyphosphates are used:

Disodium hydrogenophosphate: $Na_2HPO_4$

Pentasodium tripolyphosphate: $Na_5P_3O_{10}$

Sodium hexametaphosphate of degree of polymerization 13: $(NaPO_3)_{13}$

Sodium hexametaphosphate of degree of polymerization 25 $(NaPO_3)_{25}$

For each phosphate/polyphosphate used, two concentrations in the final solution are tested: 0.11% and 0.22%. In addition, in order to optimize the comparison between the types of phosphate/polyphosphates, the same corresponding concentrations in orthophosphates ($PO_4$) were kept for each phosphate/polyphosphate from concentration 0.11% to concentration 0.22%/

Films prepared from $(NaPO_3)_{13}$ are films F3 and F4. The other films prepared are referred to as films F6-F11. The elongations at break of the resulting films are measured in the same manner as described in Example 1. The results are collected in the following table:

| Film | Phosphate/ Polyphosphate used | Concentration of phosphate/ polyphosphate in % | Elongation at break in % | |
|---|---|---|---|---|
| | | | Sterilized by EtO | Sterilized by γ radiations |
| F6 | $Na_2HPO_4$ | 0.11 | 105.53 | 67.03 |
| F7 | $Na_2HPO_4$ | 0.22 | 97.7 | 53.90 |
| F8 | $Na_5P_3O_{10}$ | 0.11 | 112.52 | 84.16 |
| F9 | $Na_5P_3O_{10}$ | 0.22 | 109.44 | 79.19 |
| F3 | $(NaPO_3)_{13}$ | 0.11 | 110.12 | 78.45 |
| F4 | $(NaPO_3)_{13}$ | 0.22 | 118.95 | 72.34 |
| F10 | $(NaPO_3)_{25}$ | 0.11 | 116.27 | 77.66 |
| F11 | $(NaPO_3)_{25}$ | 0.22 | 212.46 | 68.93 |

These results show that films of the invention prepared from polyphosphates having a degree of polymerization ranging from 5 to 25 show an improved elongation at break with respect to films prepared from $Na_2HPO_4$.

Films of the invention prepared in the present example may be used on their own as an anti-adhesive barrier to be implanted in a patient for preventing post-surgical adhesions. Alternatively, these films may be used in combination with a prosthetic fabric in order to manufacture a composite surgical implant. For example, surgical implants for the treatment of hernia may be prepared by coating one face of a prosthetic fabric, such as a mesh, with a film of the present example. The coated film therefore serves as an anti-adhesive barrier for preventing post-surgical adhesions after implantation of the surgical implant.

The invention claimed is:

1. An implantable anti-adhesion barrier film comprising an anti-adhesive compound including both oxidized collagen and a polyphosphate compound.

2. The implantable anti-adhesion barrier film of claim 1, wherein the polyphosphate compound is represented by a general formula, $(P_nO_{3n+1})^{(n+2)}$— associated with a metal selected from the group consisting of sodium, potassium, calcium, or magnesium, wherein "n" indicates an integer between 2 and 5000.

3. The implantable anti-adhesion barrier film of claim 2, wherein the metal is sodium.

4. The implantable anti-adhesion barrier film of claim 1, wherein the polyphosphate compound is a sodium polyphosphate having a degree of polymerization ranging from 2 to 100.

5. The implantable anti-adhesion barrier film of claim 1, wherein the polyphosphate compound is a sodium polyphosphate having a degree of polymerization ranging from 2 to 25.

6. The implantable anti-adhesion barrier film of claim 1, wherein the polyphosphate compound is a sodium polyphosphate having a degree of polymerization ranging from 5 to 25.

7. The implantable anti-adhesion barrier film of claim 1, wherein the polyphosphate compound includes at least one of pentasodium tripolyphosphate ($Na_5P_3O_{10}$), sodium hexametaphosphate having a degree of polymerization of 13 $(NaPO_3)_{13}$, or sodium hexametaphosphate having a degree of polymerization of 25 $(NaPO_3)_{25}$.

8. The implantable anti-adhesion barrier film of claim 1, wherein the anti-adhesion barrier film further includes at least one of glycerol or polyethylene glycol.

9. The implantable anti-adhesion barrier film of claim 1, wherein the anti-adhesion barrier film is sterilized via ethylene oxide.

10. The implantable anti-adhesion barrier film of claim 1, wherein the anti-adhesion barrier film is non-porous.

11. The implantable anti-adhesion barrier film of claim 1, wherein the anti-adhesion barrier film is homogenous.

12. A method of preventing post-surgical adhesions in a patient comprising:

implanting an implantable anti-adhesion barrier film including an anti-adhesive compound including both oxidized collagen and a polyphosphate compound into the patient.

* * * * *